United States Patent [19]
Jakubowicz et al.

[11] Patent Number: 5,441,895
[45] Date of Patent: Aug. 15, 1995

[54] REAGENT CUP SHAPE ALLOWING STACKING WITHOUT DISLODGING REAGENT

[76] Inventors: Raymond F. Jakubowicz; Johannes J. Porte, both of Eastman Kodak Company, Rochester, N.Y. 14650

[21] Appl. No.: 163,104

[22] Filed: Dec. 7, 1993

[51] Int. Cl.6 .............. G01N 33/543; G01N 33/545; G01N 33/552
[52] U.S. Cl. .................... 436/518; 422/57; 422/58; 422/99; 422/102; 436/524; 436/527; 436/531; 436/809; 436/810
[58] Field of Search .............. 206/499, 503, 505, 515, 206/519; 422/55, 57, 58, 99, 102; 436/518, 524, 527, 531, 809, 810

[56] References Cited

U.S. PATENT DOCUMENTS

| | | | |
|---|---|---|---|
| 2,761,813 | 9/1956 | Goetz | 206/499 |
| 4,096,947 | 6/1978 | Morse | 206/519 |
| 4,260,581 | 4/1981 | Sakurada | 422/65 |
| 4,761,378 | 8/1988 | Godsey | 435/293 |
| 5,035,866 | 7/1991 | Wannlund | 436/809 |
| 5,120,503 | 6/1992 | Hinckley et al. | 422/102 |

*Primary Examiner*—David A. Saunders
*Assistant Examiner*—Christopher L. Chin
*Attorney, Agent, or Firm*—Dana M. Schmidt

[57] ABSTRACT

A stack of a plurality of substantially identical cup-like vessels pre-incorporated with reagent on the inside, each of the vessels occupying at least about 50% of the depth of the next adjacent vessel to maximize stacking density. Because the pre-incorporated reagent overlaps the occupied depth portion of the vessel and therefore runs a risk of being dislodged, the wall of the vessel is constructed to provide a gap between the inside surface bearing the reagent, and the outside surface of the occupying, nested vessel, that is at least 0.025 mm.

4 Claims, 2 Drawing Sheets

REAGENT CUP SHAPE ALLOWING STACKING WITHOUT DISLODGING REAGENT

FIELD OF THE INVENTION

This application relates to reaction vessels especially constructed to be stacked without damaging the coating of reagents inside.

BACKGROUND OF THE INVENTION

Reaction vessels have long been provided with pre-incorporated reagents. Some have even been constructed so as to be stackable, one above the other, as shown in, e.g., U.S. Pat. No. 4,761,378. However, those stacked in the '378 patent are done so without the vessels actually nesting within each other.

On the other hand, it is known to actually nest reaction vessels within each other, as shown in a wet assay analyzer described in U.S. Pat. No. 4,260,581. However, these are nestable because there is no pre-incorporated reagent—the latter is added as a liquid during assay, column 3, lines 53–63.

In fact, nesting together reaction vessels with pre-incorporated reagent is especially difficult when more than 50% of the vessel height is nested in the adjacent vessel. The reason is that, unless care is taken, the vessel inside and above can mechanically wear off the reagent in the "outer" vessel below, especially during shipment and storage. The fact that more than 50% of the vessel height is nested increases this likelihood.

RELATED APPLICATIONS

The following commonly-owned applications disclose, but do not claim, nested reaction cuvettes containing pre-incorporated reagents: U.S. Pat. No. 5,271,896 issued on Dec. 21, 1993 by R. F. Jakubowicz, J. J. Porte and R. H. Marvin, entitled "Improved Plunger and Driver Mechanism for an Analyzer", and U.S. Pat. No. 5,322,668, issued on Jun. 21, 1994 by D. A. Tomasso, entitled "Locked Bottle Holder". Spacing between nested cuvettes is not described.

SUMMARY OF THE INVENTION

This invention solves the problem of how to nest vessels whose inside surfaces do not lend themselves to the nesting principle since they are pre-incorporated with reagent.

More specifically, in accord with one aspect of the invention, there is provided a stacked plurality of reaction vessels, each of said vessels having a cup shape with an open top and an inside surface forming a closed bottom, and each having a) an outside surface effective to nest the vessel partially within an adjacent vessel so that said each vessel occupies more than 50% of the depth of said adjacent vessel, as measured from said open top, and b) a reagent pre-incorporated onto said inside surface of said each vessel at that portion of said inside surface disposed adjacent said bottom of said each vessel, the portion of each vessel that is nested within the adjacent vessel being spaced from the inside surface of said adjacent vessel by a distance that is at least 0.025 mm, so that a nested vessel does not dislodge the pre-incorporated reagent in the adjacent vessel during storage of the stacked vessels.

In accord with another aspect of the invention, there is provided a reaction vessel for stacking in a partially nested assembly with another, substantially identical, vessel, the vessel being cup-shaped with an open top, a closed bottom, and a confining wall having an inside surface and an outside surface, and further including a) a support lip on said outside surface between said top and said bottom, said lip being shaped to support the vessel on the open top of an adjacent, substantially identical vessel so that the vessel so supported extends down to occupy more than 50% of the depth of said adjacent vessel, b) a pre-incorporated reagent on said inside surface at that portion of said inside surface disposed adjacent said bottom of the vessel, and c) an inside and an outside diameter of said confining wall which extends from said closed bottom to said lip such that said outside surface, when measured transversely thereto, falls at least 0.025 mm short of the location of the inside surface of a substantially identical vessel nested adjacent to and around it, so that the vessel can be nested within said identical vessel without the pre-incorporated reagent of said identical vessel being dislodged.

Accordingly, it is an advantageous feature of the invention that reaction vessels having pre-incorporated reagents therein can be nested without dislodging those reagents.

It is a related advantageous feature that such vessels can be nested so that each occupies more than 50% of the depth of the adjacent vessel, thus saving space otherwise occupied by a stack of the vessels.

Other advantageous features will become apparent upon reference to the "Detailed Description", when read in light of the attached drawings.

DESCRIPTION OF THE PREFERRED EMBODIMENTS

As used herein, a "plurality of reaction vessels" refers to simply, more than one in association, since it requires more than one to form a partial nesting of the vessels. Clearly, it does not mean ALL the vessels in a given association, preferably a stack, must be so constructed, inasmuch as at least the top-most vessel of the stack has no other vessel nested within it, and the bottommost is not itself nested in another. Furthermore, it does not mean "all but the topmost and bottommost", since it is contemplated that non-nested vessels could be present in the stack, along with nested vessels. Hence, the invention applies, in one aspect of the invention, to a stack of reaction vessels wherein at least two are partially nested together and have the other claimed features.

The invention is described herein with regard to certain preferred embodiments, wherein the pre-incorporated reagent is an antibody or an antibody-protecting reagent such as sucrose, a buffer, or surfactants, the vessels are stacked in an analyzer, and an immunoassay is conducted within the vessel. In addition, the invention is useful regardless of the kind of reagent pre-incorporated onto the inside surface of the vessel, be it an antibody or otherwise, regardless of where the vessels are stacked, and regardless of the type of assay that uses those reagents.

Terms such as "above", "below" and the like refer to the parts when used in their assembled configuration, and especially the vessels when stacked.

Figure 1:
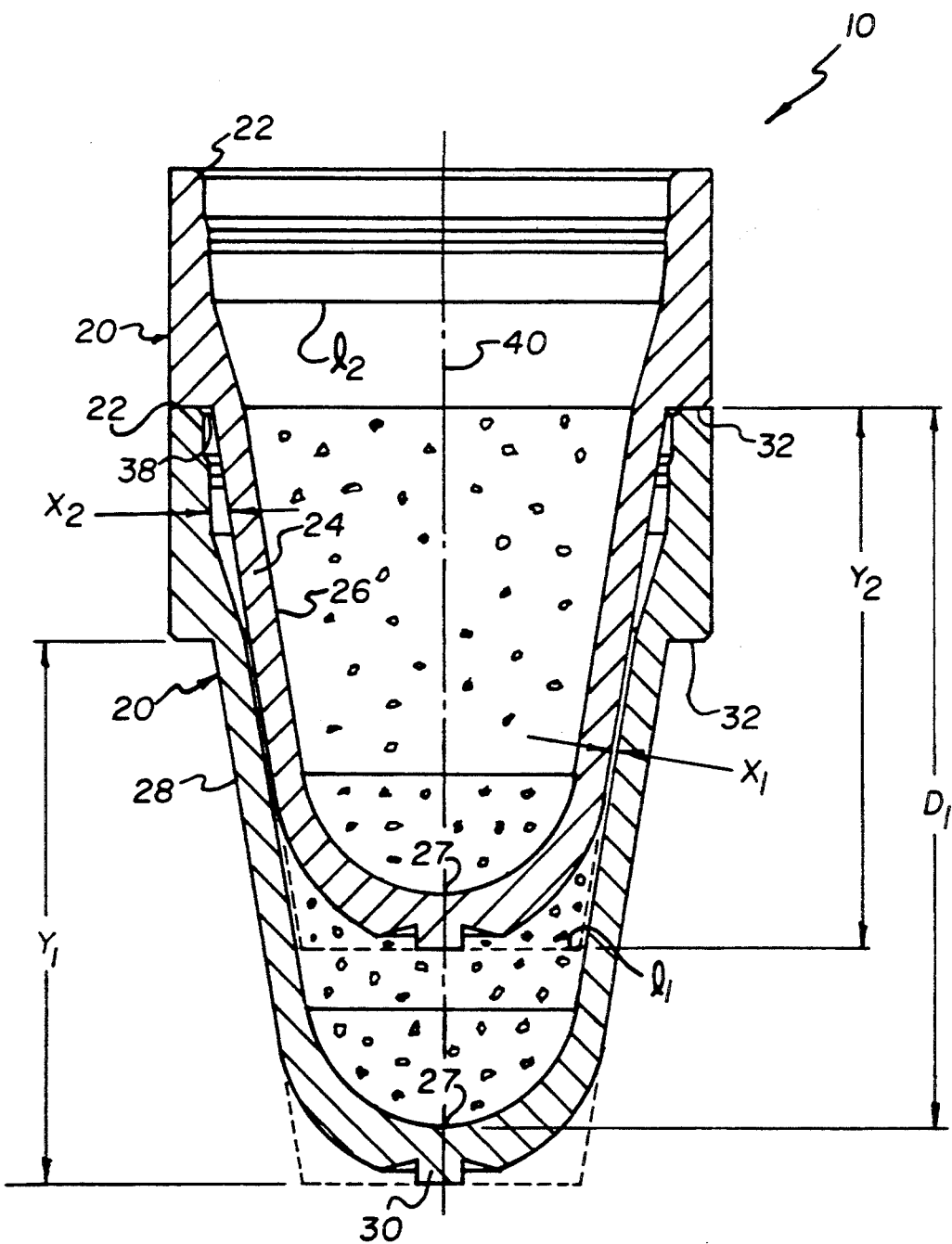
FIG. 1 is an elevational view, in section, of both a reaction vessel and a stack of such, constructed according to the invention, the vessel(s) having a certain axis of symmetry.

As shown in FIG. 1, there is provided a stack 10 of a plurality of substantially identical vessels 20, here two in number, utilizing the invention. Each vessel is cup-shaped and comprises an open top 22, a side wall 24 depending from the top and having an inside surface 26 and an outside surface 28, the side wall forming a closed bottom 30 opposite to the open top 22. Optionally, a support lip 32 is formed by recessing outside surface 28 just below top 22, lip 32 acting as the terminus of stacked insertion of each vessel into the vessel below.

The portion of outside surface 28 of side wall 24 that extends from lip 32 to bottom 30, defines along the vertical axis 40 of the stack, the occupying depth "$Y_1$" of each vessel. The portion of inside surface 26 that extends from top 22 down along axis 40 to level "$l_1$", defines the occupied depth "$Y_2$", that is, the vertical depth portion of each vessel occupied by the occupying depth $Y_1$ of the vessel above it in the stack. It is this occupied depth that is more than 50% of the total depth of the vessel $D_1$, in order to maximize the density of the stack. (For operating reasons, depth $Y_2$ is preferably, but not necessarily, no more than 80% of the total depth of the vessel.) A highly preferred value of $Y_2$ is about 70% of the total depth.

The reagent, pre-incorporated by a technique such as is disclosed hereinafter, is preferably coated in a very thin coat on inside surface 26 from the bottom point 27 of surface 26 which is the bottom of the vessel, up to but not much beyond level "$l_2$". The reagent coat is symbolized by the dots "R". Level $l_2$ can in fact be reduced to only level $l_1$, from the bottom up. However, in many cases level $l_2$ is used to ensure that enough reagent is present. In any case, the thickness of the reagent coat on inside surface 26 is generally only on the order of angstroms.

Because the occupying depth of the vessel nested above overlaps the coated surface, it is possible that the overlapped reagent can be dislodged. We have discovered that contact between surfaces 26 and 28 needs to be avoided only during storage in the stack, and not necessarily during assembly of the stack, to minimize this dislodging of the pre-incorporated reagent. To avoid such contact, vessels 20 are constructed so that, when stored as a stack, the vessels are nested with a spacing "$X_1$" between outside surface 28 of the upper vessel, and inside surface 26 of the lower vessel supporting the upper vessel, wherein "$X_1$", measured transversely to either surface, is at least 0.001 inch (0.025 mm). Most preferably, $X_1$ is about 0.075 mm. At least this spacing "$X_1$" is maintained from level $l_1$ up to top 22, or all along the occupied depth. Its maintenance is possible because the stack is preferably held, as described hereinafter, so that the nested substantially identical vessels are coaxial with axis 40, that is, each with its axis aligned with the axis of the other vessels in the stack.

Figure 2:
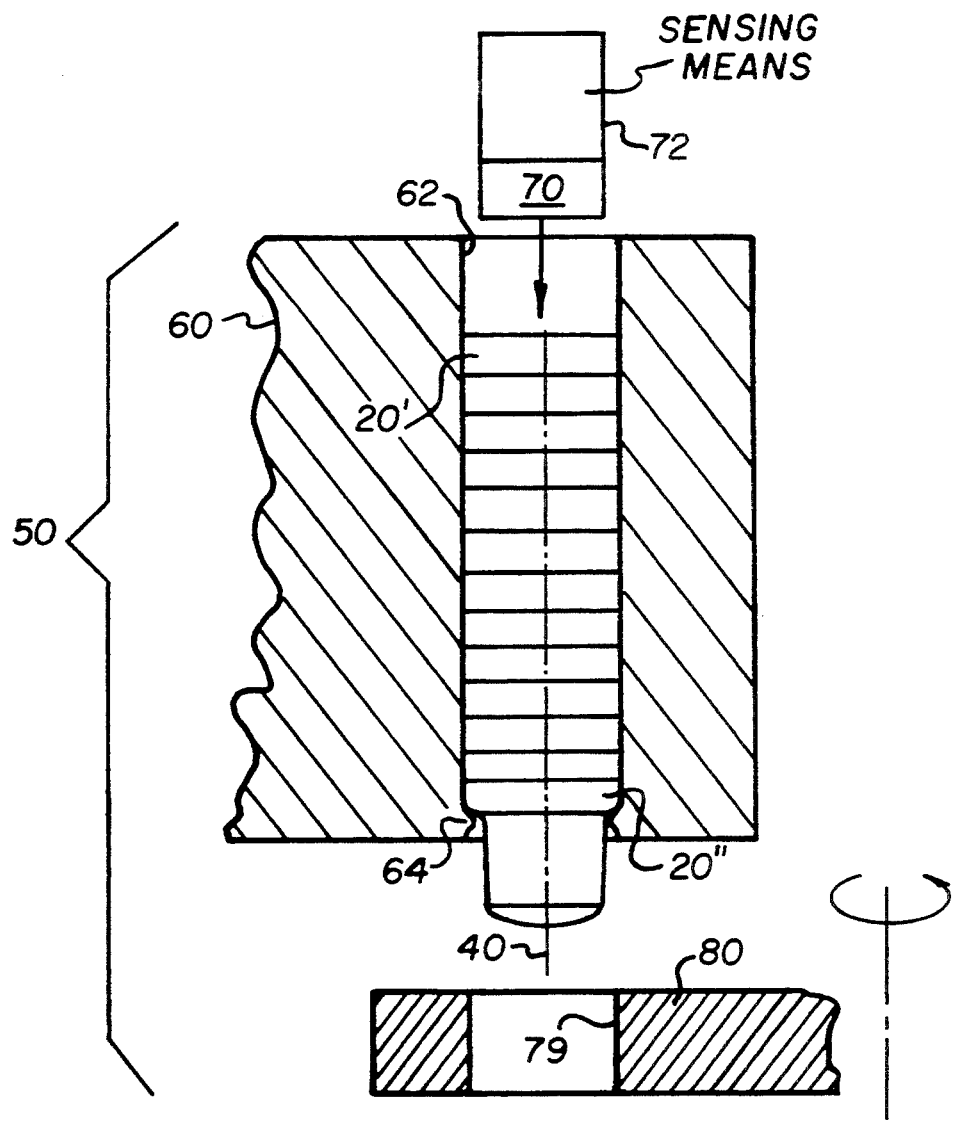
FIG. 2 is a schematic elevational view illustrating the use of such a stack.

As shown in FIG. 2, the preferred use of stack 10 is in a wet-assay analyzer 50, the other parts of which are conventional and hence not disclosed, except for module 60 that holds the stack for dispensing, a dispenser 70, and a rotor 80 which are shown in FIG. 2. Module 60 can have any external configuration and can be associated with other parts of the analyzer. Importantly, module 60 has a vertically extending bore 62 that confines stack 10 with a sliding friction fit so that each vessel in the stack is coaxial with axis 40 of the stack, as described above. The fit of vessels 20 within bore 62 should be with a tolerance less than dimension $X_1$, to ensure spacing $X_1$ is maintained. The bottom 64 of the bore is preferably provided with an inward-protruding lip or O-ring that temporarily holds up the stack and seals the stack from atmospheric contamination. Alternatively, non-continuous protrusions can be used to hold up the stack without providing an atmospheric seal.

Because the coaxial alignment of the vessels in the stack is maintained by bore 62, it is not necessary that contacting surfaces at top 22 and lip 32 be in fact complementary, although such complementary surfaces do aid in stacking the vessels during manufacturing.

Alternatively, instead of the careful tolerance given to bore 62 as noted above, the vessels' surface 26 can be extended inwardly at 38 (near top 22) to press against the outer surface of the vessel above it to properly center the latter. In that case, the tolerances of surface 26 at 38 need be less than the dimension $X_1$.

Dispenser 70 can be any device for pushing the vessels out of bore 62, one at a time. Preferably, it includes sensing means 72 to sense when dispenser 70 is in contact with top-most vessel 20' or a cap therefor in the stack, to signal that the top of the stack has been reached. Thereafter, dispenser 70 need only be advanced downwardly by a stepper motor (not shown) a distance sufficient to contact the stack and to pop bottommost vessel 20" out of lip 64 into aperture 79 of rotor 80 that transports the vessel elsewhere for processing in the analyzer.

Thus, the dispenser and sensing mechanism described in commonly-owned U.S. application Ser. No. 049,020, filed on Apr. 16, 1993 by Jakubowicz, et al entitled "Improved Plunger and Driver Mechanism for an Analyzer", now allowed, can be used. The portion that is described in that application in connection with FIGS. 4-8 thereof is expressly incorporated herein by reference.

Most preferably, the pre-incorporated reagent is an antibody to an antigen to be assayed by the analyzer. Such antibodies are well-known, as are the chemistries for binding them to a wall surface, so that further description is unnecessary, except to say that, for example, the antibodies to the hCG or TSH antigen can be used. Further, the pre-incorporation is preferably achieved by depositing an aqueous solution of the antibodies (about 180 μL, for example) in the vessel. The following is a preferred procedure, using the methods described by Cart and Tregear in *Science*, Vol. 158, p. 1570 (1967):

The antiserum is diluted in a weak buffer at the isoelectric point of the antibodies (typically pH 8 to 9) and left for a period to adsorb onto the surface of the plastic vessels. The antibodies may be purified before use if desired but this is not essential. The plastic vessels are washed with a buffer solution at about the same pH containing protein (typically bovine serum albumin), and additionally sodium chloride and/or detergent together with other additives which improve the stability of the antibody coated onto the surface (typically lactose or sucrose). The protein is to cover any areas of the plastic surface which are not coated with antibody, and the sodium chloride and detergent remove any loosely bound antibody from the surface. After washing, the vessels are dried in a draft of air and stored in dry conditions at 2°-8° C.

It may be advantageous to expose the antibodies to a low pH or to urea before coating in order to improve the adsorption of the plastic.

A simple specific method for coating vessels would be as follows:

Mix 64 mls antiserum to CEA (carcinoembryonic antigen) raised in sheep with 18 liters of 10 mM TRIS buffer containing 19.4 gram tris(hydroxymethyl) methylamine and adjusted to pH 9.0 with 1M hydrochloric acid. Dispense 200 microliters into the plastic vessels. Incubate 16 hours at 20° C. Aspirate the coating solution from the vessels and wash by filling and emptying the vessels four times with 100 mM TRIS buffer containing 4235 gram tris(hydroxymethyl)methylamine, 1925 gram bovine serum albumin in 350 liters of water adjusted to pH of 8.5 with 5M hydrochloric acid. Dry the vessels in a draft of air at 28° C.

Importantly, when applying the reagent, the solution should not contact wall 26, FIG. 1, above level $l_2$ and clearly not top 22, as otherwise it can cause sticking of top 22 to lip 32 of the next adjacent vessel.

Other configurations of wall 24 are possible for vessels 20. For example, bottom 30 need not be rounded as shown, but can be "squared off" as shown in phantom.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A stacked plurality of reaction vessels, each of said vessels having a cup shape with an open top and an inside surface forming a closed bottom, and each comprising
   a) an outside surface shaped sufficiently to nest the vessel partially within an adjacent vessel so that said each vessel occupies more than 50% of the depth of said adjacent vessel, as measured from said open top of said adjacent vessel, and
   b) a reagent pre-incorporated onto said inside surface of said each vessel at a portion of said inside surface disposed adjacent said bottom of said each vessel,
   a portion of each vessel that is nested within the adjacent vessel being spaced from the inside surface of said adjacent vessel by a distance that is at least 0.025 mm.

2. A stacked array as defined in claim 1, wherein said reagent is an antibody immobilized on said inside surface.

3. A reaction vessel for stacking in a partially nested assembly with another vessel substantially identical to said reaction vessel, said reaction vessel being cup-shaped with an open top, a closed bottom spaced from said open top, and a confining wall having an inside surface and an outside surface between said open top and closed bottom, and further including
   a) a support lip on said outside surface between said top and said bottom, said lip being shaped to support said reaction vessel on the open top of said another substantially identical vessel so that said reaction vessel so supported extends down to occupy more than 50% of the depth of said adjacent vessel,
   b) a pre-incorporated reagent on said inside surface at a portion of said inside surface disposed adjacent said bottom of said reaction vessel, and
   c) an inside and an outside diameter of said confining wall which extends from said closed bottom to said lip such that said outside surface, when measured transversely thereto, falls at least 0.025 mm short of any location of an adjacent inside surface of said another substantially identical vessel nested adjacent to and around said reaction vessel,
   so that said reaction vessel can be nested within said another vessel without the pre-incorporated reagent of said another vessel being dislodged.

4. A vessel as defined in claim 3, wherein said reagent is an antibody immobilized on said inside surface.

* * * * *